United States Patent
Borsari et al.

(10) Patent No.: US 9,937,213 B2
(45) Date of Patent: Apr. 10, 2018

(54) COMPOSITION COMPRISING L. RHAMNOSUS GG

(71) Applicant: GRANAROLO S.P.A., Bologna (IT)

(72) Inventors: Andrea Borsari, Bologna (IT); Vittorio Angelo Zambrini, Bologna (IT)

(73) Assignee: GRANAROLO S.P.A., Bologna (BO) (IT)

( * ) Notice: Subject to any disclaimer, the term of this patent is extended or adjusted under 35 U.S.C. 154(b) by 0 days.

(21) Appl. No.: 14/900,159

(22) PCT Filed: Jun. 26, 2014

(86) PCT No.: PCT/IB2014/062619
§ 371 (c)(1),
(2) Date: Dec. 20, 2015

(87) PCT Pub. No.: WO2014/207690
PCT Pub. Date: Dec. 31, 2014

(65) Prior Publication Data
US 2016/0143964 A1 May 26, 2016

(30) Foreign Application Priority Data

Jun. 28, 2013 (IT) .............................. MI2013A1083

(51) Int. Cl.
| | | |
|---|---|---|
| A61K 35/00 | (2006.01) | |
| A61K 35/747 | (2015.01) | |
| A23C 9/13 | (2006.01) | |
| A23C 9/123 | (2006.01) | |
| A23L 33/00 | (2016.01) | |
| A23L 33/135 | (2016.01) | |

(52) U.S. Cl.
CPC .......... *A61K 35/747* (2013.01); *A23C 9/1232* (2013.01); *A23C 9/1234* (2013.01); *A23C 9/1307* (2013.01); *A23L 33/135* (2016.08); *A23L 33/40* (2016.08); *A23V 2002/00* (2013.01); *A23Y 2220/73* (2013.01); *A61K 2035/115* (2013.01)

(58) Field of Classification Search
CPC .............. A61K 2300/00; A61K 35/742; A61K 35/745; A61K 35/747; A61K 35/74; A61K 35/744; A61K 31/496; A61K 31/704; A61K 31/7048; A61K 45/06; A61K 31/43; A61K 31/545; A61K 31/65; A61K 38/14; A61K 47/44; A61K 9/001; A61K 2035/115; A61K 9/0034; A61K 9/0014; A61K 31/63; A61K 31/7034; A61K 38/00; A61K 38/164; A23V 2002/00; A23V 2200/302; A23V 2200/304; A23V 2200/324; A23C 9/1232; A23C 9/1234; A23C 9/1307; A23Y 2220/73; A23L 1/296; A23L 1/3014; A23L 33/135; A23L 33/40
See application file for complete search history.

(56) References Cited

U.S. PATENT DOCUMENTS

| | | | |
|---|---|---|---|
| 8,697,055 B2 * | 4/2014 | Farmer ................ | A61K 31/496 |
| | | | 424/93.45 |
| 2003/0180260 A1 | 9/2003 | Clancy et al. | |
| 2009/0035294 A1 | 2/2009 | Mahe et al. | |

FOREIGN PATENT DOCUMENTS

WO        2012057636 A1    5/2012

OTHER PUBLICATIONS

Oktay Yerlikaya, "Starter cultures used in probiotic dairy product preparation and popular probiotic dairy drinks" Food Sci. and Tech. 34(2): 221-229, Apr.-Jun. 2014.*
Morita et al, "Complete Genome Seq. of the Probiotic Lactobacillus rhamnosus ATCC 53103", J. of Bacteriology, Dec. 2009, p. 7630-7631.*
Ananta E., et al., "Cellular Injuries and storage stability of spray-dried Lactobacillus rhamnosus GG", International Dairy Journal, Elsevier Applied Science, Barking, GB, vol. 15, No. 4, Apr. 1, 2005, pp. 399-409.
Database GNPD (Online) Mintel: Aug. 2011 Anonymous: "Natural Drinking Yogurt", database accession No. 1609277.
Database GNPD (Online) Mintel: Dec. 1998 Anonym: "Culturelle", database accession No. 69630.
Database GNPD (Online) Mintel: Feb. 2009 Anonymous: "Balance Nutrition", database accession No. 1047324.
Database GNPD (Online) Mintel: Jun. 2011 Anonymous: "3+ Nutritional Supplement for Babies with Low Appeptite", database accession No. 1554694.
Database GNPD (Online) Mintel: May 2013 Anonymous: "Cultured Milk with Apricots", database accession No. 2083209.
International Search Report of PCT/IB2014/062619 dated Nov. 27, 2014.
Kekkonen R.A., "Immunomodulatory effects of probiotics", Australian Journal of Dairy Technology, Dairy Industry Association of Australia, Melbourne, AU, vol. 64, No. 1, Feb. 1, 2009, pp. 128-132, "Systematic Investigation of the immunomodulatory effects of probiotics"; p. 130.
Khani, et al., "413-8670/ in vitro study of the effect of a probiotic bacterium Lactobacillus rhamnosus against herpes simplex virus type 1", Baz. J. Infect. Dis. Mohammad Motamedifar, Jan. 1, 2012, retrieved from Internet.
Leblanc J. G., et al, "Bacteriocin producing lactic acid bacteria isolated from Boza, a traditional fermented beverage from Balkan peninsula—from isolation to application" In: "Science against microbial pathogens: communicating current research and technological advances", Jan. 1, 2011, pp. 1311-1320.

(Continued)

*Primary Examiner* — Debbie K Ware
(74) *Attorney, Agent, or Firm* — Silvia Salvadori, P.C.; Silvia Salvadori

(57) ABSTRACT

The present finding relates to a composition comprising the probiotic *Lactobacillus rhamnosus* GG (ATCC 53103) for use in the prevention and/or treatment of herpes labialis and to a composition comprising the probiotic bacterial species and a soluble prebiotic fiber.

6 Claims, 5 Drawing Sheets

(56) References Cited

OTHER PUBLICATIONS

Oh, M., et al., "Antiviral activity of *Lactobacillus* spp. and polysaccharide", Journal of Bacteriology and Virology 2010 Chonnam National University Medical School Kor, vol. 40, No. 4, 2010, pp. 145-150.
Todorov S.D., et al., "Boza, a natural source of probiotic lactic acid bacteria", Journal of Applied Microbiology, vol. 0, No. 0, Oct. 8, 2007, p. 470-471.
Written Opinion of International Searching Authority of PCT/IB2014/062619 dated Nov. 27, 2014.

* cited by examiner

COMPOSITION COMPRISING *L. RHAMNOSUS GG*

This application is a U.S. national stage of PCT/IB2014/062619 filed on 26 Jun. 2014, which claims priority to and the benefit of Italian Application No. MI2013A001083 filed on 28 Jun. 2013, the contents of which are incorporated herein by reference in their entireties.

The present finding relates to a composition comprising *Lactobacillus rhamnosus* GG (filed and identified as ATCC 53103) for use in the prevention and/or treatment of herpes labialis, and to a composition comprising this probiotic strain and at least one soluble prebiotic fibre.

Herpes labialis is a common disorder resulting from the presence of herpes simplex virus (HSV-1). Due to its visibility, herpes labialis has a relevant impact on social life and psychological well-being of people suffering from this disorder. Furthermore, it has been reported (Pebody et al. Sex Transm Infect 2004;80:185-191) that cases of other forms of herpes, such as genital, caused by HSV-1, are increasing.

Generally, the infection is transmitted during childhood. In one study carried out in seven European countries (Pebody et al. ibidem), it was found that seropositivity ranges from 52% in Finland to 84% in Bulgaria. In one study carried out in Italy, seropositivity to HSV-1 was 51.6% at the age of 11 and 6.4% at the age of 17 (Suligoi et al. Sex Transm Dis 2004, 31:608-10). From this study, it appeared that incidence was higher among the female population and equal to 1.6 per 100 people/year, i.e. 1.6 cases of HSV-1 are expected every 100 people studied in one year.

In addition to physical discomfort and itching, due to its visibility, herpes labialis has a relevant impact on social life and psychological well-being of people suffering from this disorder. Furthermore, the virus can remain present in the subject in a latent form after the first infection, and can reactivate in the presence of triggering factors such as cold, solar exposure, physical and/or psychic stress, giving origin to recurrences of herpes labialis. Currently, the only available treatment is the pharmacological one (antivirals, such as acyclovir) that has limited efficacy and requires many topical applications at the time when the lesion is apparent. The disease is considered chronic and impossible to cure in a definitive way. No treatments exist that can prevent possible recurrences of the disorder.

One object of the present finding is to provide a composition able to prevent and treat herpes labialis, at the time when the subject has warning symptoms of the appearance of herpes outbreak.

Another task of the present finding is to provide a composition able to prevent herpes labialis outbreaks in a subject that has frequent recurrences of herpes over the year.

Another task of the present finding is to provide a composition efficient against herpes labialis, and HSV-1 in general, in a form that can be readily taken by subjects of any age and basically free from side effects.

According to the present finding, these and other objects that will be better apparent hereinafter, are achieved through a composition comprising *Lactobacillus rhamnosus* GG for use in the prevention and/or treatment of herpes labialis, wherein said use comprises oral intake of the composition by a subject.

According to the present finding, these objects were further achieved through a milk product, in the form of a beverage, solid, semi-solid/creamy product, powder or granulate, comprising *Lactobacillus rhamnosus* GG and at least one soluble prebiotic fibre selected from a FOS (fructo-oligosaccharide), a galacto-oligosaccharide (GOS), inulin, polydextrose, galactofructose (lactulose), an arabinogalactan, a xylo-oligosaccharide (XOS), a resistant starch (to human enzymatic digestion) or mixtures thereof.

According to the present finding, these objects were further achieved through a dry preparation in the form of an orally soluble or water-dispersible powder or granulate, comprising *Lactobacillus rhamnosus* GG and at least one soluble prebiotic fibre selected from a FOS (fructo-oligosaccharide), a galacto-oligosaccharide (GOS), inulin, polydextrose, galactofructose (lactulose), an arabinogalactan, a xylo-oligosaccharide (XOS), a starch resistant to human enzymatic digestion or mixtures thereof. Within the scope of the present invention, by probiotic organism a viable microorganism is meant that, if administered in a suitable amount, provides a benefit to the host's health ("Guidelines on probiotics and prebiotics" Italian Ministry of Health, revised May 2013, and FAO document "Report of a Joint FAO/WHO Expert Consultation on Evaluation of Health and Nutritional Properties of Probiotics in Food Including Powder Milk with Live Lactic Acid Bacteria" October 2001).

In order to be considered as probiotics, microorganisms must fulfil the following requirements:
- being safe for human use: probiotic microorganisms should not carry acquired and/or transmittable antibiotic-resistances;
- being active and viable on an intestinal level, in an amount such that explains possible beneficial effects observed in efficacy studies;
- being able to convey a demonstrated physiological benefit.

Within the scope of the present invention, by prebiotic a non-digestible and non-assimilable by humans food compound is meant that, if taken in a suitable amount, conveys a benefit to the body, thanks to a selective promotion of growth and/or activity of one or more bacteria, already present in the intestinal tract or taken simultaneously with the probiotic.

The definition of prebiotic is based on selective non-digestibility and fermentability by some bacterial groups, without posing any limitation to the chemical nature, even though most used prebiotics are carbohydrates.

Within the scope of the present invention, probiotics and prebiotics can be taken in different ways, for example as additional or constitutive ingredients of food or food supplement.

Within the scope of the present invention, by milk product a preparation for human consumption is meant, to be taken by oral route and containing at least one ingredient completely or partially derived from milk processing. Non limiting examples of milk products, within the scope of the present invention, are milk (also pasteurized, whole or half- or completely skimmed), fermented milk, yoghurt, soft or hard cheese, or liquid or semi-liquid beverages, that are milk-based or comprise milk derivatives, or whey-based, optionally flavoured with flavourings or other food ingredients. The abovementioned products can also be in a dry form.

Other food matrixes free from milk and derivatives thereof ("dairy free") suitable to carry the active ingredients of the present invention for the prevention of recurrences of herpes labialis are listed hereinafter: products derived from fruit, such as juices, purees, fruit-based beverages; products derived from cereals such as e.g. beverages based on oat, rice, barley, etc.; products derived from nuts e.g. beverages based on almonds, walnuts, etc.

Within the scope of the present invention, by a starch resistant to human enzymatic digestion, the starch fraction is meant, that resists to the hydrolytic process (digestion) by the digestive enzymes of the small intestine. Non limiting examples are native or resistant starches derived from cereals.

Within the scope of the present invention, by dry preparation a preparation other than food, that is, having no nutrition purposes is meant, in the form of a powder or granulate. Examples of said dry preparations can be a food supplement or a pharmaceutical or nutraceutical preparation.

If not otherwise specified, within the scope of the present invention, percentages are meant to be referred to the weight of one component on the total weight of the composition.

Figure 1:
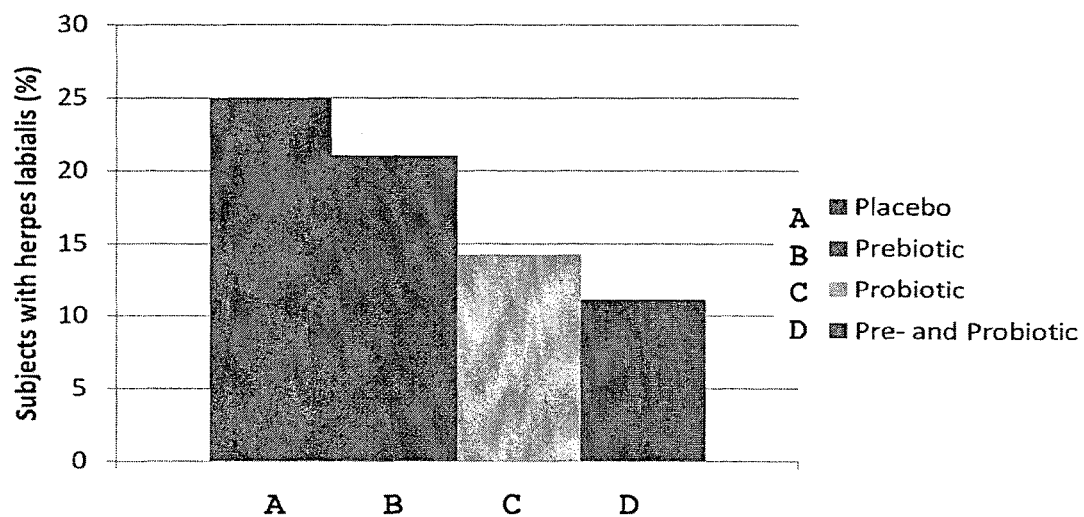
FIG. 1 depicts the presence of lesions of herpes labialis after 35 days in the "intention to treat" (ITT) population expressed as the percentage of subjects with herpes labialis.

In one aspect, the present invention relates to a composition comprising *Lactobacillus rhamnosus* GG for use in the prevention and/or treatment of herpes labialis, wherein said use comprises oral intake of the composition by a subject.

*Lactobacillus rhamnosus* GG (ATCC 53103), a strain belonging to the species *L. rhamnosus*, but first referred to as *Lactobacillus acidophilus*, was first identified in 1983 by Sherwood Gorbach and Barry Goldin of the Tufts University of Boston, from whom it was given the initials GG.

It is one of the first bacteria that demonstrated to be able to survive in and colonize the human gastrointestinal tract. It is known that the ability of colonizing the gastrointestinal tract allows this probiotic bacterium to exert a protecting action against infections, to keep the intestinal balance. Despite this colonization is not permanent, the presence of *L. rhamnosus* GG in the intestine can be ensured through constant administration of compositions containing the bacterium; if discontinued, ferments remain present and active in the intestine at least for the subsequent two weeks.

*Lactobacillus rhamnosus* GG fulfils all the requirements set in order to be defined a probiotic:

it stands gastric and bile acids, usually disadvantageous factors for bacteria, and remains viable and active along all the digestive tube;

it adheres to the intestinal epithelium, where it inhibits the action of pathogenic bacteria;

it becomes a natural component of the intestinal microflora, balancing it;

through the improvement of the intestinal mucosal barrier, it modulates the immune response and contributes to natural defences.

To date, hundreds of studies have been published illustrating the properties of *L. rhamnosus* GG and its effects on allergy remission, on rebalancing the intestinal microflora and its metabolism, and on the improvement of permeability of the intestinal mucosa, of immune response, and on the decrease of side effects of antibiotics. It is additionally known that *L. rhamnosus* GG reduces atopic dermatitis in early childhood, infantile and traveller's diarrhoea in countries with poor hygienic conditions, and respiratory and gastrointestinal tract infections. However, so far the effect of administration by oral route of *L. rhamnosus* GG on HSV-1 infections has never been disclosed.

Within the scope of the present invention, it was surprisingly found that administration of *Lactobacillus rhamnosus* GG by oral route (i.e. as a beverage or food) can be used as a treatment for HSV-1 infections, in particular in the presence of herpes labialis, and to prevent recurrences.

In one clinical study on people prone to recurrent herpes labialis (example 1) the effects of the administration of a milk product comprising *Lactobacillus rhamnosus* GG by oral route (with or without FOS) on the appearance of herpes labialis were observed, in comparison with a "placebo" milk product containing neither *Lactobacillus rhamnosus* GG nor the prebiotic FOS.

It resulted that administration, at least once daily, of a dairy product comprising *Lactobacillus rhamnosus* GG (in this specific case a "minidrink" in a liquid form, comprising fermented milk and this probiotic) is efficient in the prevention and/or treatment of the onset of herpes labialis following exposure to a triggering factor (exposure to UV radiations without protection). In fact, in the group of patients taking *L. rhamnosus* GG (with or without FOS) by oral route, a decrease both in the presence of lesions of herpes labialis and in the appearance of new lesions (incidence) of herpes labialis, and an increase of the percent PMN cells that phagocyte and kill *Candida* were observed.

These effects on herpes labialis by probiotics (optionally in association with prebiotics) were observed for the first time with the composition of the present invention.

The invention comprises *L. rhamnosus* GG for use in the prevention and/or treatment of herpes labialis, wherein said use includes oral intake of the composition by a subject prone to outbreaks of herpes labialis. Optionally, the present invention comprises *L. rhamnosus* GG for use in the prevention and/or treatment of herpes labialis, wherein said use comprises its oral intake simultaneously with other substances and/or active ingredients.

"By oral route" means the intake by a subject by mouth, i.e. by gastroenteral route, and not by topical application on the buccal mucosa. For example, the composition according to the invention can be taken by the subject in the form of food, beverage, food supplement or as a pharmaceutical form, for example as a tablet, capsule, orally soluble granulate, solution or suspension of a powder in water, fruit juice, milk and similar liquids.

In a preferred embodiment, the composition comprising *L. rhamnosus* GG for use in the treatment and/or prevention of herpes labialis according to the present invention additionally comprises at least one soluble prebiotic fibre selected from a FOS, a galacto-oligosaccharide (GOS), inulin, polydextrose, galactofructose (lactulose), an arabinogalactan, a xylo-oligosaccharide, a starch resistant to human enzymatic digestion or mixtures thereof. More preferably, the composition for use according to the present invention comprises Lactobacillus rhamnosus GG and FOS.

Preferably, the composition for use according to the present invention is taken as a milk product in the form of a beverage, or as a dry preparation in the form of an orally soluble or water-dispersible powder or granulate (e.g. in water, fruit juice, milk, tea, at room temperature).

In a preferred embodiment, for the use according to the invention, an amount of L. rhamnosus GG between $1\times10^9$ and $100\times10^9$ cfu (colony forming units) is taken by oral route daily. More preferably, the amount of L. rhamnosus GG taken daily is comprised between $2\times10^9$ cfu and $5\times10^9$ cfu. These total amounts can be taken by the subject on a daily basis, in one or two doses.

The intake can occur at any time of the day, preferably simultaneously with breakfast, on an empty stomach, or before a meal.

In another aspect, the present invention comprises a milk product, in the form of a beverage, solid, semi-solid, or an orally soluble or water-dispersible powder or granulate, comprising L. rhamnosus GG and at least one soluble prebiotic fibre selected from a FOS, a galacto-oligosaccharide (GOS), inulin, polydextrose, galactofructose (lactulose), an arabinogalactan, a xylo-oligosaccharide (XOS), starch resistant to human enzymatic digestion or mixtures thereof.

In another aspect, the present invention relates to a dry preparation in the form of an orally soluble or water-dispersible powder or granulate, comprising L. rhamnosus GG and at least one soluble prebiotic fibre selected from a FOS, a galacto-oligosaccharide (GOS), inulin, polydextrose, galactofructose (lactulose), an arabinogalactan, a xylo-oligosaccharide (XOS), a starch resistant to human enzymatic digestion, or mixtures thereof.

The granulate or powder comprising L. rhamnosus GG and at least one soluble prebiotic fibre according to the present invention can be taken by direct dissolution in the subject's oral cavity or after dissolution/suspension in an aqueous phase such as water, milk, fruit juice, tea or similar preparations at room temperature or at the desired temperature, lower than about 40° C. As non limiting examples, the milk product of the invention can be in the form of whole, skimmed or half-skimmed milk, optionally pasteurized or submitted to another thermal treatment, yoghurt, beverage based on fermented milk, solid or semi-solid cheese. Preferably, in the milk product according to the present invention the content of L. rhamnosus GG is between $1\times10^9$ and $100\times10^9$ cfu and/or the content of soluble prebiotic fibre is between 1 g and 6 g. More preferably, in the milk product according to the present invention the content of L. rhamnosus GG is of $2\times10^9$ cfu and the content of soluble prebiotic fibre is of 3 g.

In a preferred embodiment, in the milk product or in the dry preparation according to the present invention, the soluble prebiotic fibre is FOS.

The milk product or the dry preparation according to the present invention can comprise additional ingredients such as flavours, sweeteners, stabilizers, anti-agglomerating agents, acidity regulators, colourings.

Non limiting examples of excipients that can be comprised in the milk product or dry preparation according to the invention are: maltodextrins, dextrose, lactose, magnesium stearate, silicon dioxide, flavours.

Preferably, the milk product according to the invention comprises fermented milk with a fat content lower than 4 g/100 g of product.

Preferably, in the milk product or dry preparation according to the present invention, L. rhamnosus GG can be present in a lyophilized form (in the case of a powder or a product in a solid form) or in a microencapsulated form able to improve its survival, also depending on the resistance to gastric and digestive acids and on the storage duration. As a non limiting example, the shell of the microcapsule comprising L. rhamnosus GG in the milk product or dry preparation according to the present invention can comprise alginate.

Preferably the milk product or dry preparation according to the present invention comprises at least another bacterial species with a probiotic action.

In addition to Lactobacillus rhamnosus GG, the milk product or dry preparation according to the invention can comprise also other probiotic bacterial species promoting the balance of the intestinal microflora and/or intestinal well-being such as (in a not exhaustive way): Bifidobacterium longum, Bifidobacterium breve, Bifidobacterium animalis, Bifidobacterium bifidum, Lactobacillus acidophilus, Lactobacillus reuteri, Lactobacillus casei, Lactobacillus delbrueckii subsp. bulgaricus or mixtures thereof. Additions of the above microorganisms can be such that, in one single dose (1 sachet), they provide an amount of each bacterial species ranging from 1 to 50 billion cfu per single dose, so that the other bacterial species added are present in the final product in an amount lower than or equal to that of Lactobacillus rhamnosus GG. Biomasses of the bacterial species can be freeze-dried products, as such or microencapsulated, depending on their resistance to gastric and digestive juices and storage duration.

One embodiment of the present invention is described hereinafter in an example, by way of illustration and not of limitation.

EXAMPLE 1

Objects of the Clinical Study in Humans

Evaluation of the effect of Lactobacillus rhamnosus GG administration (with or without FOS) on incidence and progression of herpes labialis.

A secondary object of the study is to evaluate the effect of L. rhamnosus GG administration (with and without FOS) on specific immune responses against HSV.

The study was carried out as a single centre, randomized, triple blind, placebo-controlled study.

Subjects are selected among the healthy population, between 18 and 65 years of age, with recurrent herpes labialis (no more than three episodes after exposure to sunlight in the last 12 months) but without apparent herpes labialis at the time of enrolment. Subjects do not show any intolerance to milk proteins and/or lactose, and have not consumed probiotics and prebiotics for at least one month before the beginning of the study, do not take acyclovir or other active ingredients with effects on the immune system at the time of the study, have not participated in studies involving reactivation of HSV-1 through UV radiations in the previous three months and have not shown episodes of herpes labialis for at least 30 days before the beginning of the study.

At time zero ("run in", day 0) the sensitivity of each subject to ultraviolet light was evaluated, for the determination of the minimal erythema dose (MED), by irradiating the forearm with a UV lamp at a distance of 19 cm for 1, 2, 3, 4, 5 and 6 min. The power of irradiation was measured with a manual exposure meter in mW/cm$^2$ and kept constant. Subjects that had not developed a reaction after 6 min of exposure are excluded from additional studies. The so determined MEDs were used to define the time of UV exposure necessary to develop a lesion of herpes labialis. On the same day, designated subjects received the first batch of "placebo" (pasteurized fermented milk without active ingredients) and took the first dose. After a period of 14 days ("baseline"), subjects underwent a blood draw, and they were randomly assigned to one of the four groups that received, anonymously and in double blind, the following products: pasteurized fermented milk (placebo); fermented milk supplemented with the prebiotic FOS; fermented milk supplemented with the probiotic Lactobacillus rhamnosus GG; fermented milk supplemented with Lactobacillus rhamnosus GG and FOS.

Baseline characteristics of the population and the respective exposure times to UV radiations are as follows:

Group 1—placebo: age (years) 47±14; number of subjects: 20 (men/women 10/10); BMI (kg/m$^2$) 24±3; exposure to UV rays (sec) 118±9; compliance to protocol 99.5%.

Group 2—"Prebiotic" (only FOS): age (years) 44±10; number of subjects: 20 (men/women 10/10); BMI (kg/m$^2$) 24±3; exposure to UV rays (sec) 120±10; compliance to protocol 100%.

Group 3—"Probiotic" (L. rhamnosus GG): age (years) 47±16; number of subjects: 21 (men/women 8/13); BMI (kg/m$^2$) 24±3; exposure to UV rays (sec) 120±9; compliance to protocol 100%.

Group 4—"Prebiotic and Probiotic" (L. rhamnosus GG and FOS): age (years) 42±14; number of subjects: 18 (men/women 8/10); BMI (kg/m$^2$) 23±2; exposure to UV rays (sec) 121±9; compliance to protocol 99.7%.

All data are expressed as mean±standard deviation.

Exposure to UV radiations occurred after 19 days of intake of the different abovementioned products (day 33) according to the procedure of Evans T. G. et al. 2002 Antimicrob Agents Chemother 2002; 46: 1870-1874.

During the exposure procedure, the half of the lips (upper, lower lip or right/left part of both lips) that is considered most prone to recurrence of herpes labialis was exposed to UV radiations for a time equal to four times the MED. The remainder of the lips and the surrounding skin are protected with a filter containing p-aminobenzoic acid with SPF of at least 30.

About 44% of subjects are expected to develop a lesion between 48 hours and 7 days after exposure to UV radiations (Sayre R. M. et al. Photodermatol Photoimmunol Photomed. 2007, 23 (1):20-33).

Two days (day 35) and seven days (day 42) after exposure to UV radiations, subjects were clinically examined to look for any signs of herpes lesions. The end of study visit, comprising the final blood sample draw, was performed on day 49.

During all the period each subject has to fill in a questionnaire on the following topics: questionnaire on the epidermis type according to Fitzpatrick, self-evaluation of the herpes lesion, questionnaire on the quality of life (SF 36), adverse events, protocol deviations (compliance) and indication of food to be limited or avoided during the whole study (food rich on fibres and/or containing probiotics).

No subject withdrew from the study after being assigned to one of the four groups.

The placebo beverage consists of fermented (via addition of yoghurt specific ferments), and then pasteurized to inactivate the microorganisms, low-fat (half-skimmed) milk, without addition of L. rhamnosus GG and FOS.

The beverage comprising probiotics and/or prebiotics consists of half-skimmed, fermented milk to which Lactobacillus rhamnosus GG and/or FOS were added. All doses have a net weight of 90 g (single daily dose).

Their composition is reported in Table 1 (g/100 g of individual ingredients).

TABLE 1

| Product | Placebo | Enriched with L. rhamnosus GG | Enriched with FOS | Enriched with FOS and L. rhamnosus GG |
|---|---|---|---|---|
| Energy (kcal) | 75 | 75 | 73 | 73 |
| Fat | 1.9 | 1.9 | 1.9 | 1.9 |
| Saturated fats (SAFA) | 1.2 | 1.2 | 1.2 | 1.2 |
| Carbohydrates | 11.0 | 11.0 | 10.7 | 10.7 |
| Proteins | 2.8 | 2.8 | 2.7 | 2.7 |
| FOS Fibres | — | — | 3.1 | 3.1 |
| Sodium | 0.05 | 0.05 | 0.05 | 0.05 |
| L. rhamnosus GG × 10$^6$ cfu/g | 0 | 20 | — | 20 |
| FOS | — | — | 3.1 | 3.1 |

Each group took the specific assigned product, from day 14 to day 49.

Subjects took 90 g of the assigned product every day at breakfast. Placebo and products comprising L. rhamnosus GG and/or FOS have the same consistency, taste and smell.

Clinical evaluation of the results was performed via visual inspection of the irradiated surface, measurement of the lesions (in mm), time necessary for healing, defined as loss of the stiff scab or return to the normal appearance of epidermis (in days), development of the lesion (progressively scored as prodromic, erythema, papula blister, ulcer or soft scab, stiff scab, normal skin), duration and intensity of the pain scored by the patient on a visual analogic scale.

The evaluation of the specific immune response to HSV-1 was quantified through analysis of plasma levels of specific IgG1, IgG3, IgG4, IgE to HSV-1, through specific measurements with the ELISA method.

The compliance to protocol (compliance) in the study is high, almost 100%, in the four study groups.

Presence of Lesions of Herpes Labialis

Figure 2:
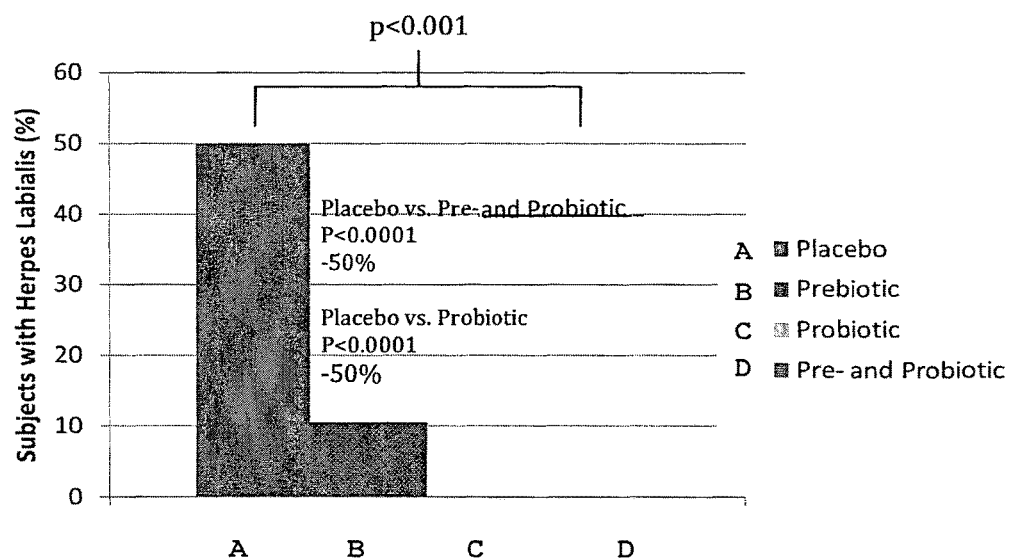
FIG. 2 depicts the presence of lesions of herpes labialis after 42 days in the "intention to treat" (ITT) population expressed as the percentage of subjects with herpes labialis.
Figure 3:
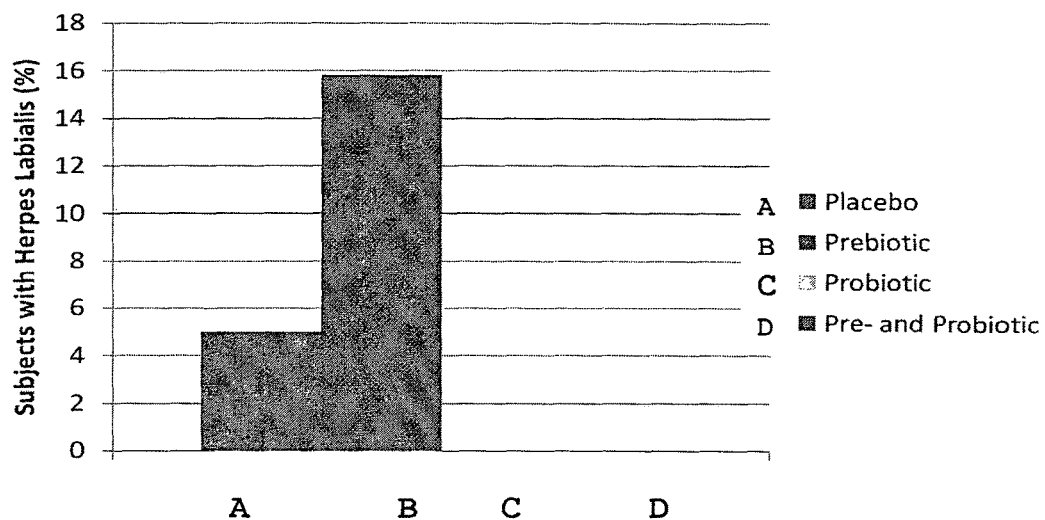
FIG. 3 depicts the presence of lesions of herpes labialis after 49 days in the "intention to treat" (ITT) population expressed as the percentage of subjects with herpes labialis.

In FIGS. 1 to 3 the presence of lesions of herpes labialis is shown in the four study groups after exposure to UV radiation in the intention to treat population (ITT), i.e. all those who started the treatment, regardless of the fact that they terminated it.

At visit 5 (day 42) 10 subjects (50.0%) that had consumed the placebo beverage showed the presence of a lesion, as compared with two subjects (10.5%) that had consumed the prebiotic minidrink and none of the subjects of the other two groups, that had consumed a beverage containing L. rhamnosus GG according to the present invention.

The analysis showed a statistically significant difference between placebo group and both probiotic minidrink and pre- and probiotic combination (p<0.0001). Also at the following visit, on day 49, in the two groups that had consumed fermented milk containing L. rhamnosus GG there are no subjects having outbreaks of herpes labialis.

Incidence of Lesions of Herpes Labialis

Figure 4:
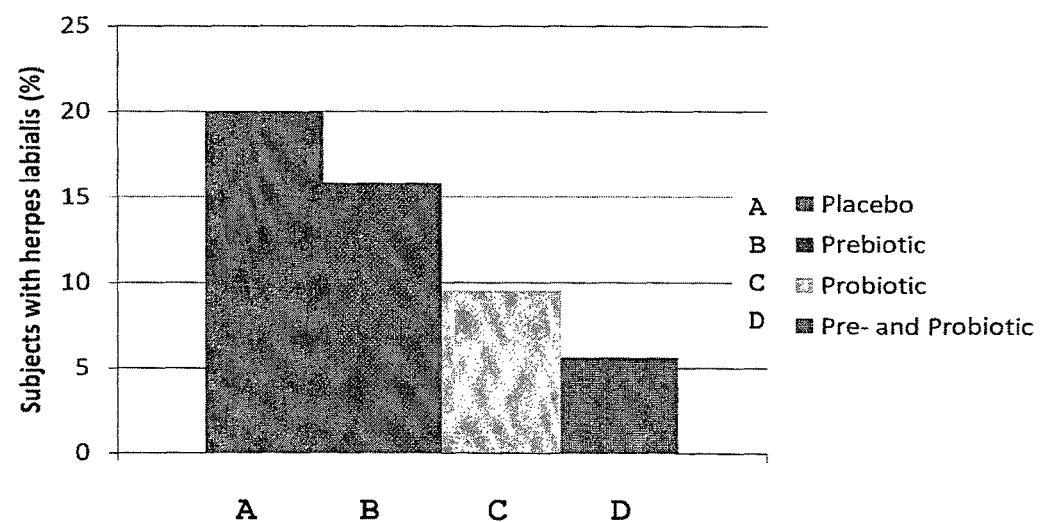
FIG. 4 depicts the presence of new lesions of herpes labialis in the "intention to treat" (ITT) population after 35 days expressed as the percentage of subjects with herpes labialis.
Figure 5:
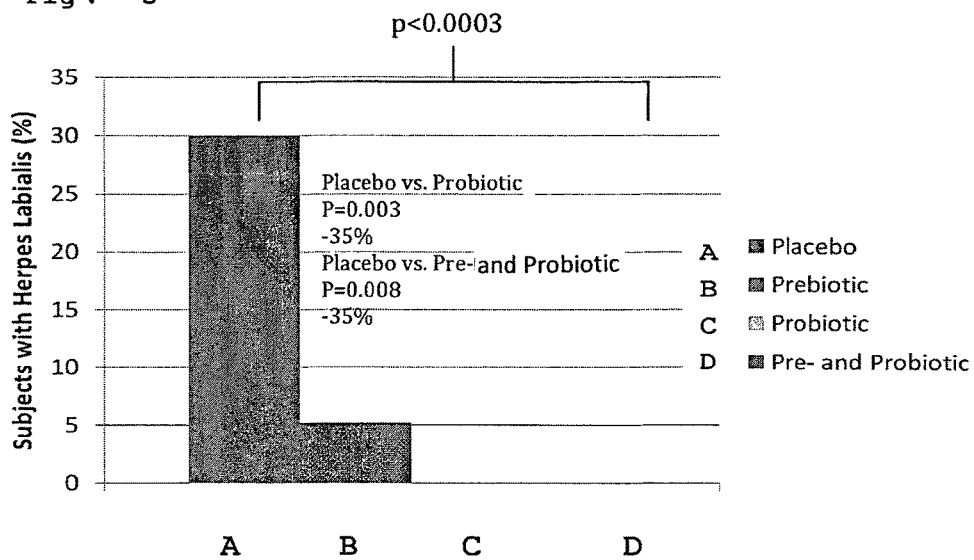
FIG. 5 depicts the presence of new lesions of herpes labialis in the "intention to treat" (ITT) population after 42 days expressed as the percentage of subjects with herpes labialis.
Figure 6:
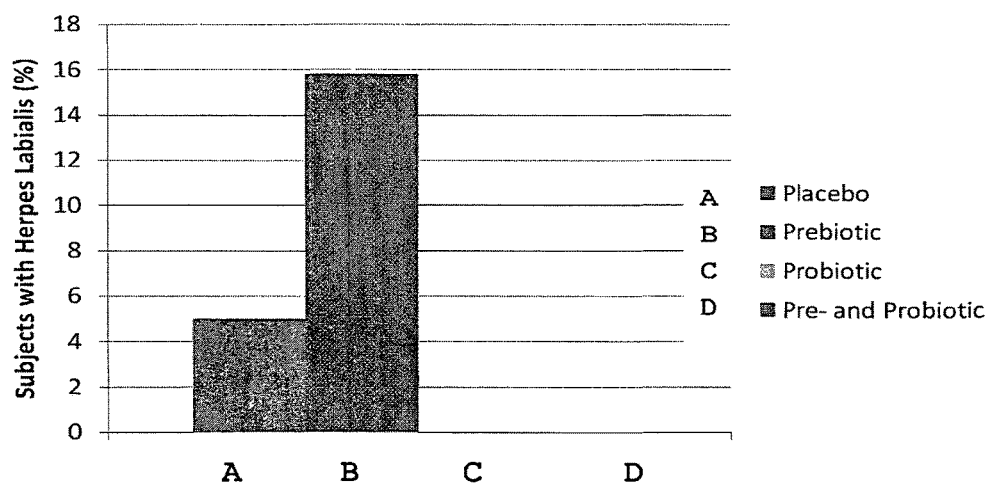
FIG. 6 depicts the presence of new lesions of herpes labialis in the "intention to treat" (ITT) population after 49 days expressed as the percentage of subjects with herpes labialis.

Concerning the appearance of a new lesion (incidence of lesions of herpes labialis) after exposure to UV radiations, results are reported in FIGS. 4 to 6.

On day 35, subjects with new lesions were 4 (20.0%) in the placebo group, 3 (18.7%) in the prebiotic group, 2 (9.5%) in the probiotic group and only 1 (5.5%) in the prebiotic and probiotic group.

On the other hand, on day 42, new lesions were present in 7 subjects (35.0%) that had consumed the placebo beverage and in 1 subject (5.2%) that had consumed the prebiotic; no new lesions were observed in the probiotic group and in that consuming the prebiotic and probiotic combination.

A statistically significant difference (level 0.008) is present between the placebo group (P=0.003) and both the probiotic group and the pre- and pro-biotic group (P=0.008).

Effects on the Immune System

Figure 7:
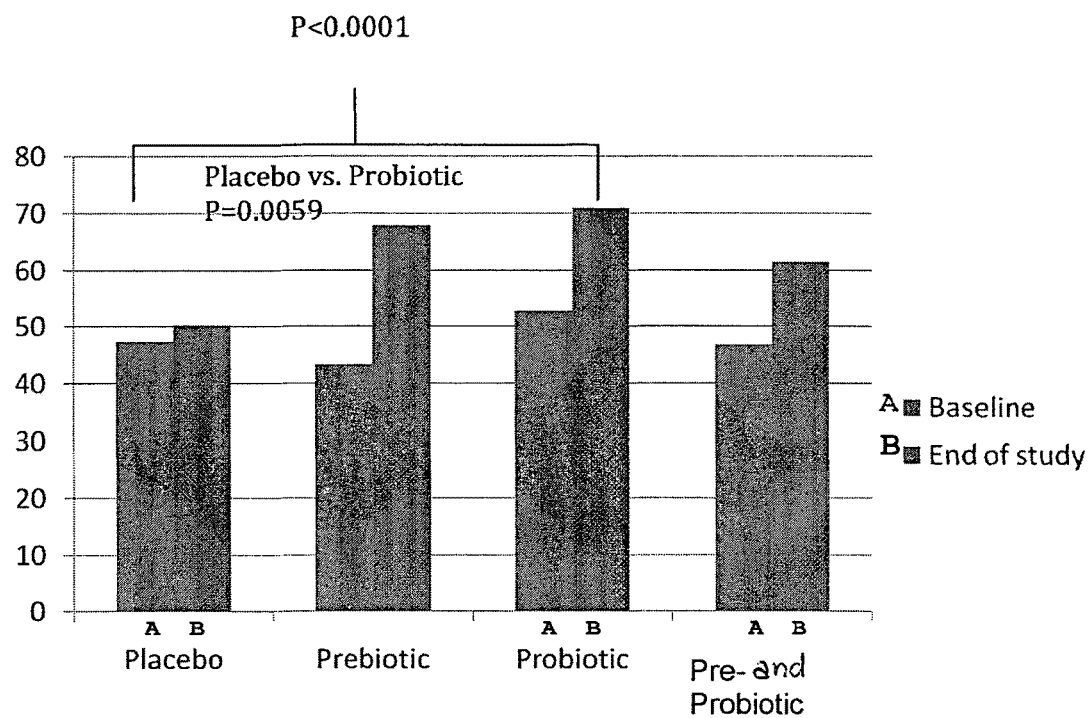
FIG. 7 shows the percentage of PMN able to phagocytise and kill *Candida* that actually phagocyte *Candida*.
Figure 8:
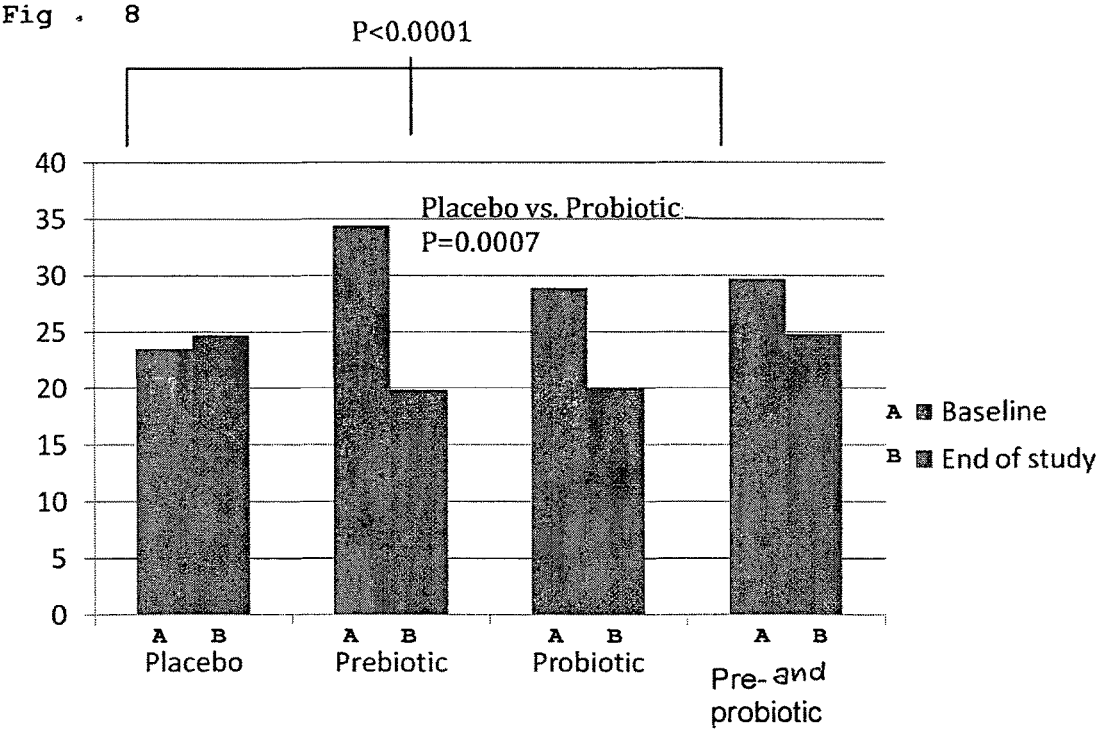
FIG. 8 shows the percentage of PMN able to phagocytise and kill *Candida* that do not kill *Candida*.
Figure 9:
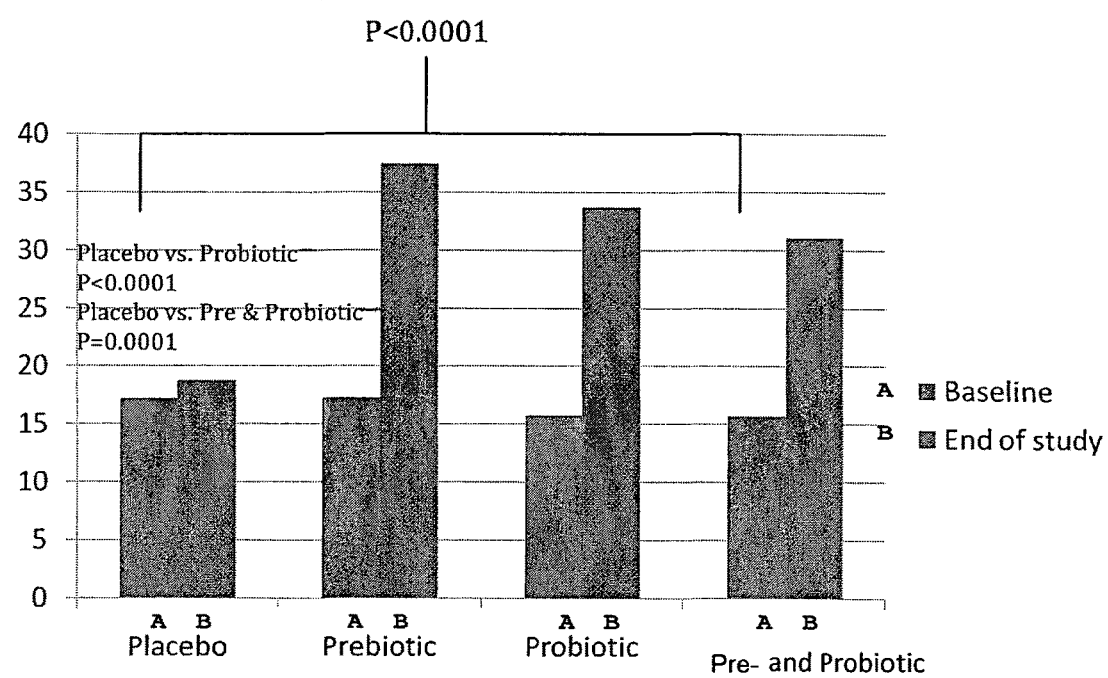
FIG. 9 shows the percentage of PMN able to phagocytise and kill *Candida* that actually kill *Candida*.

In FIGS. 7 to 9, effects on the innate immune system parameters are represented. Concerning the phagocytosis activity carried out by polymorphonuclear cells (PMN) obtained from blood drawn from the subjects, on the microorganism Candida used as a target, a significant difference was found between the components of the placebo group and the groups that had taken fermented milk supplemented with L. rhamnosus GG, and that with L. rhamnosus GG supplemented with FOS.

Adverse Events

Only one non-serious adverse event was reported in the probiotic group, i.e. symptoms of influenza, which appeared to be an episode of bronchitis.

The present study demonstrates that daily consumption of a minidrink according to the invention, containing either Lactobacillus rhamnosus GG alone or a combination of Lactobacillus rhamnosus GG and fructo-oligosaccharides, decreases in a significant manner both presence and incidence of lesions of herpes labialis after stimulation with UV radiation in a population with recurrent herpes labialis. This is the first study that demonstrates the efficacy of a minidrink containing probiotics or a combination of pre- and probiotics in a population with reactive herpes simplex virus-1.

The reactivation mechanism of the herpes simplex virus, with consequent infection, is not completely known. Several studies suggest that various biological intersubject variations, such as phagocytosis and destruction by polymorphonuclear cells (PMN), activity of natural killer cells, number of CD8 cells, production of cytokines, such as interferon-γ, are important in resistance to reactivation of the virus. In this study, no difference was found in the function of both CD8+T lymphocytes and natural killer cells. However, a tendency that did not reach statistical significance, was observed for some immunological analyses, which could suggest a modulation effect of the product comprising probiotic or the product comprising prebiotic and probiotic on the adaptive immune system. Results of the analyses of the immune system at the end of the study were slightly improved as compared with baseline values in subjects taking "minidrinks" with prebiotics and/or probiotics, however differences between groups did not reach the required level of statistical significance. The small number of enrolled individuals in the four experimental groups (total 78) may explain these results.

However, phagocytosis and destruction are clearly and statistically different in subjects that used placebo or minidrinks. Then:

1) the three minidrinks were significantly better in increasing the percentage of PMN cells that phagocyte Candida, in comparison with placebo;

2) the three minidrinks were significantly better in decreasing the percentage of PMN cells that phagocyte Candida, but do not kill Candida (non-killer cells), in comparison with placebo; and 3) the three minidrinks were significantly better in increasing the percentage of PMN cells that phagocyte Candida and kill Candida, in comparison with placebo. Hence, minidrinks containing prebiotics and probiotics have an important effect on innate immunity, with a consequent significant improvement of both phagocytosis and destruction (pathogen killing). A recent publication (Cermelli C. et al. Microbiol. Immunol. 2008 December; 52(12): 575-584) demonstrates that HSV-1 infection prevents monocyte activation, then leading to significant impairment of the monocyte-mediated anti-Candida response. The observation that minidrinks containing prebiotics and/or probiotics can positively modulate this parameter is biologically important and can be the explanation of the occurrence of beneficial effects of the test compounds on lesions of herpes labialis.

CONCLUSION

The consumption of a minidrink containing the probiotic Lactobacillus rhamnosus GG or a minidrink containing a combination of Lactobacillus rhamnosus GG and fructo-oligosaccharides reduces appearance and incidence of recurrent herpes labialis. This is the first study to show an effect of probiotics or a combination of pre- and probiotics in a population with HSV-1 with outbreaks of herpes labialis.

The invention claimed is:

1. A method for the prevention and/or treatment of herpes labialis, comprising daily and orally administering alive Lactobacillus rhamnosus GG ATCC 53103 in an amount of between $1\times10^9$ cfu and $100\times10^9$ cfu to a subject suffering from recurrent herpes labialis.

2. The method according to claim 1, wherein said alive Lactobacillus rhamnosus GG ATCC 53103 is contemporaneously orally administered in association with at least one soluble prebiotic fibre selected from a fructo-oligosaccharide (FOS), a galacto-oligosaccharide (GOS), inulin, polydextrose, galactofructose (lactulose), an arabinogalactan, a xylo-oligosaccharide, a starch resistant to human enzymatic digestion, or mixtures thereof.

3. The method according to claim 1, wherein said alive Lactobacillus rhamnosus GG ATCC 53103 is orally administered in the form of a composition selected from
   a) a milk product in the form of a beverage, a solid, a semi-solid/creamy product, powder or granulate, or
   b) a dry preparation in the form of an orally soluble or water-dispersible powder or granulate, wherein said milk product (a) or dry preparation (b) comprises at least one soluble prebiotic fibre selected from a fructo-oligosaccharide (FOS), a galacto-oligosaccharide (GOS), inulin, polydextrose, galactofructose (lactulose), an arabinogalactan, a xylo-oligosaccharide, a starch resistant to human enzymatic digestion, or mixtures thereof.

4. The method according to claim 3, wherein the content of soluble prebiotic fibre is between 1 g and 6 g.

5. The method according to claim 3, wherein said milk product (a) or dry preparation (b) contains FOS as soluble probiotic fibre.

6. The method according to claim 3, wherein said milk product (a) or dry milk product (b) containing Lactobacillus rhamnosus GG ATCC 53103 is contained in microcapsules.

* * * * *